United States Patent [19]

Heusser

[11] Patent Number: 4,862,741
[45] Date of Patent: Sep. 5, 1989

[54] TEXTILE STRAND TESTER

[75] Inventor: Eduard Heusser, Uster, Switzerland

[73] Assignee: Zellweger Uster AG, Uster, Switzerland

[21] Appl. No.: 116,784

[22] Filed: Nov. 5, 1987

[30] Foreign Application Priority Data

Nov. 7, 1986 [CH] Switzerland ............... 04459/86
Nov. 7, 1986 [CH] Switzerland ............... 04460/86

[51] Int. Cl.⁴ .................................. G01L 5/04
[52] U.S. Cl. ............................... 73/160; 73/159
[58] Field of Search ............ 73/160, 159; 19/293, 19/287; 28/126–135, 224, 227

[56] References Cited

U.S. PATENT DOCUMENTS

| | | | |
|---|---|---|---|
| 54,732 | 5/1866 | Hussey | 19/293 |
| 2,810,936 | 10/1957 | Altenburger | 19/293 |
| 3,788,138 | 1/1974 | Heusser | 73/160 |
| 4,075,744 | 2/1978 | Mista et al. | 28/227 |
| 4,536,971 | 8/1985 | Pulsmeier et al. | 73/159 |

FOREIGN PATENT DOCUMENTS 219332 12/1924 United Kingdom ............... 19/293

Primary Examiner—William M. Shoop, Jr.
Assistant Examiner—Brian Young
Attorney, Agent, or Firm—Burns, Doane, Swecker & Mathis

[57] ABSTRACT

The apparatus contains a feed device for the material to be tested, which feed device is formed by a pair of transport rollers (16). Both transport rollers are positively connected to a motor drive. Perfect forward feed of the material is thereby ensured under all conditions and careful treatment of the test material is also ensured, a factor which is particularly advantageous if further measurements are to be carried out on the test material after it has passed through the feed device.

As the test material passes through the transport rollers, a traverse motion along the axes of the transport rollers (16) takes place between said rollers and the material to be tested. This ensures very uniform wear on the transport rollers, which in turn ensures smooth forward movement of the material in all circumstances. It also ensures that the path of movement of the thread does not vary during the measuring process.

19 Claims, 4 Drawing Sheets

TEXTILE STRAND TESTER

FIELD OF THE INVENTION

This invention relates to an apparatus for the automatic determination of characteristic magnitudes of textile material to be tested, such as yarns, rovings and slivers. It is concerned particularly with strand testing apparatus of the type in which the strand is drawn through a test zone by a pair of rollers engaging the strand from opposite sides as the strand passes therebetween.

BACKGROUND

In textile laboratories, especially of spinning mills, spot checks are carried out on random samples by way of quality control to determine certain textile parameters such as fluctuations in weight and other characteristic quantities which can be derived from these measurements. These tests are carried out by means of so called uniformity testers of the kind, for example, which are distributed world wide by Zellweger Uster AG under the registered trademark of USTER.

Typically a uniformity tester includes a measuring unit containing a guide device, a measuring instrument, a feed device and a draw-off device for the sample to be tested. The feed device is formed by a pair of transport rollers. In the measuring instrument, the strand is sensed while passing through one of a plurality of measuring gaps each of which constitute the air gap of a capacitor and the aforesaid magnitudes are measured capacitively.

To determine the fluctuations in weight of the material being tested, the material is pulled through the measuring comb by the transport rollers and is removed by suction by the draw off device after the test. The rate of feed is up to 400 meters per minute for test material consisting of staple fibres and up to 800 meters per minute for filament yarns. Under these conditions, perfect operation of the transport rollers is of major importance.

In the known uniformity testers, one of the two transport rollers is motor driven while the other is driven by friction with the driven roller or, in the case of thick test material, it is driven by way of this material. The roller which is not actively driven therefore always rotates more slowly than the driven roller. The difference in the circumferential speeds of the two rollers depends on the fineness of the material being tested. The operator therefore has to deal with undetectable variations in speed which lead to unreliable or false measurement results.

Another factor which influences the rate of feed of the test material is the extent to which the transport rollers, which are made of a hard rubber-like material, have undergone wear. In the known uniformity testers, a manually operated guide web is provided to prevent the wear on the rollers always taking place in the same position as this could lead to the formation of grooves. The position of this guide web should be adjusted by the operator before each test so that the material to be tested will always pass through the nip between the rollers at a different point.

Apart from the fact that this displacement of the guide web does not ensure that the transport rollers will wear uniformly, the displacement is not always carried out regularly by the operators.

OBJECTS AND SUMMARY OF THE INVENTION

An object of the present invention is to so improve the test material feeding capability of a uniformity tester that correct forward feed of the material is ensured under all conditions and so that the test material is treated very carefully, a factor which is particularly important if measurements are to be carried out on the material downstream of the feed device.

Another object of the present invention is to improve the known uniformity tester so as to ensure as far as possible uniform wear of the transport rollers so that the test material will be transported smoothly in all circumstances.

In accordance with the invention the strand material to be tested is passed between and contacted from opposite sides by a pair of transport rollers each of which is positively rotated by suitable drive means. This assures that there will be no unexpected differences between the surface speeds of the two rollers which would have a tendency both to damage the test material and to induce measurement errors or inconsistencies. In a preferred form, provision is made for separation of the two positively rotated transport rollers from one another to facilitate insertion of test material therebetween. Also, additional features preferably are provided to uncouple the rollers upon the occurrence of undesired build up of test material.

In accordance with another aspect of this invention, the transport rollers are given a back and forth traverse motion relative to the path of the test material therebetween to cause the wear on the roller surfaces to be spread out along the roller length and thereby guard against the development of irregularities that would adversely affect the measuring capabilities of the equipment.

BRIEF DESCRIPTION OF THE DRAWINGS

The invention will now be described with reference to an exemplary and the accompanying drawings, in which.

DETAILED DESCRIPTION OF PREFERRED EMBODIMENTS

Figure 1:
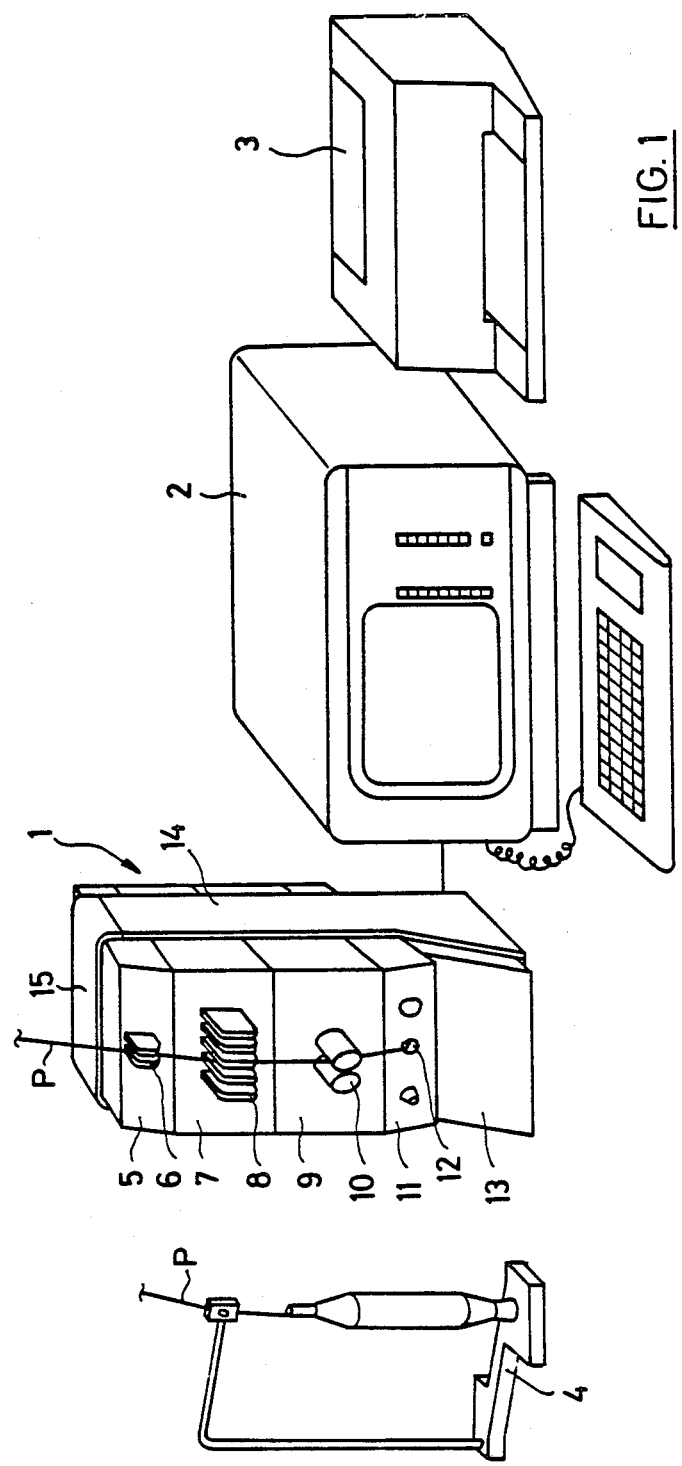
FIG. 1 is a view in perspective of a uniformity tester for determining the fluctuations in weight of staple fibre yarn.

The uniformity tester illustrated in FIG. 1 for determining fluctuations in weight of textile material to be tested, such as yarns, rovings or slivers of staple fibres, comprises, as illustrated, a measuring unit 1, an interpreting unit 2, an output element 3 and a framework 4 for the packages of test material P, such as spools of yarns or rovings. Uniformity testers of this type are known and are distributed worldwide by Zellweger Uster AG under the trademark USTER.

The measuring unit 1 for the test material P consists, as illustrated, of several modules which are arranged in the following order in the direction of travel of the test sample P, i.e. from above downwards in the drawing:

first, a module 5 provided with a thread guiding device 6, for example a thread brake; then module 7 equipped with a measuring instrument 8; followed by a module 9 carrying a feed device 10; and finally a module 11 with a draw off suction nozzle 12. The lowermost module 11 is mounted on a base 13 and all the aforesaid modules 5, 7, 9 and 11 together with the base 13 are fitted into a frame 14 having a stirrup-shaped upper part 15 and are held by this frame.

The measuring instrument 8 through which the test sample P is drawn by the feed device 10, which consists of a pair of rollers, is a so called capacitive measuring instrument. This has been described in U.S. Pat. No. 3,754,172; 3,788,138; and 3 805 607; the disclosures of which are incorporated herein by reference. The draw off suction nozzle 12 is already known from the above mentioned USTER tester and need not be described here.

The interpreting unit 2 contains inter alia an analog-to-digital converter and a computer and is combined with a display screen, as shown. The electric signals continuously produced by the measuring instrument 8 are processed by the computer of the interpreting unit 2 and stored in some suitable form in a memory integrated with the interpreting unit 2 and may be displayed on the screen before being printed out on the output unit 3. This has the advantage that all data obtained may first be displayed on the screen and only selected data need be printed out by the printer 3.

It should be noted that the signal processing device in the interpreting unit 2 has three main components, namely a spectrograph for the so called spectrogram (wave length spectrum of fluctuations in weight), an imperfection indicator, which counts the excesses of weight above the limiting value, and an interpreting part proper for determining the so called variation coefficients and the length variation graph. All these parameters are already known from the USTER tester mentioned above.

If the uniformity tester is required to determine fluctuations in weight of filament yarns, the measuring unit 1 must have a different construction which differs from the unit 1 shown in the drawing in several respects. A different measuring instrument particularly appropriate for filament yarns is required, although this is again a capacitive measuring instrument. Instead of locating the feed device 10 downstream of the measuring instrument 8, it should be arranged upstream of the measuring instrument 8 when filament yarns are to be tested. Also, a special draw off suction nozzle is required impart to the filament yarn the twist required for the test. For details of this type of suction nozzle, see U.S. Pat. No. 3,951,321, the disclosure of which is incorporated herein by reference.

The measuring unit 1 may be provided with additional modules so that it may also be used for determining other parameters of the test material P. Thus, for example, an additional module equipped with an instrument for measuring the hairiness of the test material P may be inserted so that both the hairiness and the fluctuations in weight of the sample P may be determined in a single passage through the measuring unit 1. For such a measuring unit, see Swiss Patent Application No. 02 823/86-2 in the name of the assignee of the present patent application.

Figure 2:
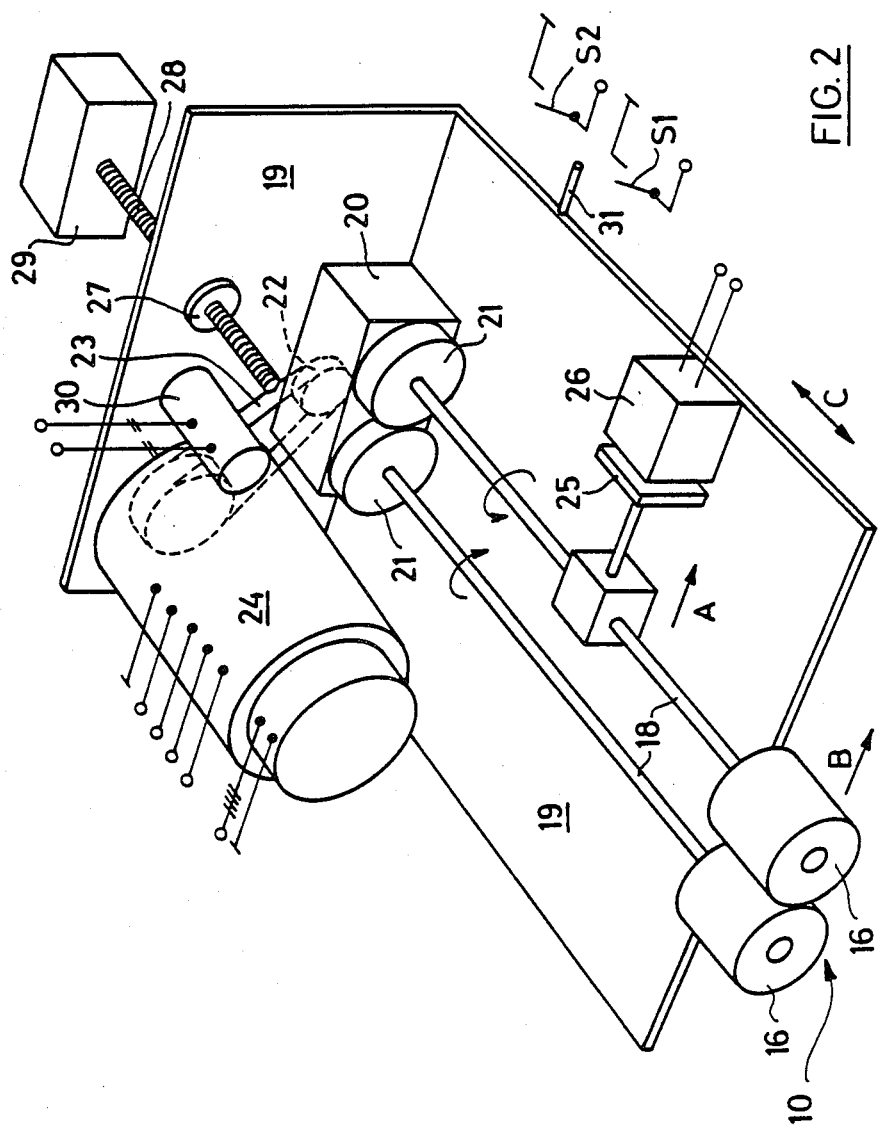
FIG. 2 is a view in perspective of the essential parts of the measuring instrument of the measuring unit of the uniformity tester.

FIG. 2 shows an overall view in perspective of the main parts of the feed device 10 of the measuring unit 1 of the uniformity tester of FIG. 1. This is formed, as illustrated, by a pair of transport rollers 16 of a material having the characteristics of hard rubber mounted at the end of two motor driven shafts 18. The shafts 18 are mounted in a bearing block 20 which in turn is mounted on an L-shaped support plate 19, and each shaft 18 carries a gear wheel 21. The two gear wheels 21 engage with one another and are connected to a belt pulley 22 which is connected to a drive motor 24 by a toothed belt 23. Both transport rollers 16 are thus positively connected to the drive motor 24.

The two transport rollers 16 touch one another when at rest. When in operation, the distance between them depends on the thickness of test material. Insertion of the test material into the measuring unit 1 (FIG. 1) is carried out by means of an insertion arm (not shown) which grips hold of the test material P and places it into the thread guiding device 6, into the measuring instrument 8 and between the transport rollers 16 and presents it to the suction nozzle 12 (FIG. 1). The transport rollers 16 are designed to be swung away from one another to facilitate automatic insertion of the test material.

For this purpose, a displacement device 25 in the form of a ram is attached to one of the two shafts 18, the right hand shaft in the drawing, and this device 25 is associated with an electromagnet 26 and is drawn to the electromagnet 26 when the latter is energized. The shaft 18 with its displacement device 25 is thereby moved in the direction of the arrow A and the right hand transport roller 16 is deflected away from the left hand transport roller in the direction of the arrow B so that a gap is formed between the two transport rollers for insertion of the test material. To ensure that the gear wheels 21 will not disengage at the same time, at least the shaft 18 with the displacement device 25 but preferably both shafts 18 are flexible over part of their length. Instead of the right hand shaft being displaceable, the left hand shaft 18 or both shafts 18 could, of course, be displaceable.

A threaded element 27 engaging with a threaded spindle 28 is rotatably mounted on the rear wall of the L shaped support plate 19. The threaded spindle 28 is held at one end on a part 29 which is firmly fixed in the measuring unit 1 (FIG. 1). The element 27 is internally threaded to cooperate with the threaded spindle 28 and is connected to a driving motor 30 and so as to be rotated when this motor is switched on. The supporting plate 19 with all the parts fixed thereto then moves relatively to the part 29 in the direction of the double arrow C in one or the other direction, depending on the direction of rotation. In particular, the transport rollers 16 execute a stroke in the direction of the longitudinal axes of the shafts 18.

The support plate 19 is arranged in a housing containing the module 9 (FIG. 1), and the two transport rollers 16 project from the front plate of this housing. Since the test material P is stretched between the thread guiding device 6 and the draw off suction nozzle 12 (FIG. 1), it makes contact with the two transport rollers 16 at some specified point between the two most closely adjacent generatrixes of the surfaces of the rollers. When the two transport rollers 16 execute the above mentioned stroke in the direction of the arrow C, the test material slides along this generatrix and executes a traverse motion relative to the transport rollers. The path taken by the thread therefore does not change during the measuring process.

When the measuring unit 1 (FIG. 1) is in operation, the two drive motors 24 and 30 are continuously actuated and the transport rollers 16 execute both rotation and longitudinal displacement (arrow C). The longitudinal displacement of the support plate 19 and hence of the transport rollers 16 is limited by a laterally projecting actuating device 31 on the support plate 19 and two end switches Sl and S2 arranged in the path of movement of the device 31. When the threaded element 27 is driven in such a direction that the support plate 19 and the transport rollers 16 move forward out of the position illustrated, the actuating device 31 makes contact with the switch Sl is actuated and thereby reverses the sense of rotation of the drive motor, and the support plate 19 and transport rollers 16 are then displaced in the opposite direction, i.e. rearwardly. This continues to take place until the end switch S2 is actuated by the actuating device 31 which again reverses the sense of rotation of the drive motor 30, and so on.

The longitudinal displacement of the transport rollers 16 and the traverse motion of the test material thus take place continuously and fully automatically and the arrangement is so designed that one complete stroke, i.e. one forward and return movement of the transport rollers 16 with a stroke length of about 25 millimeters per half stroke takes place in about four minutes.

Figure 3:
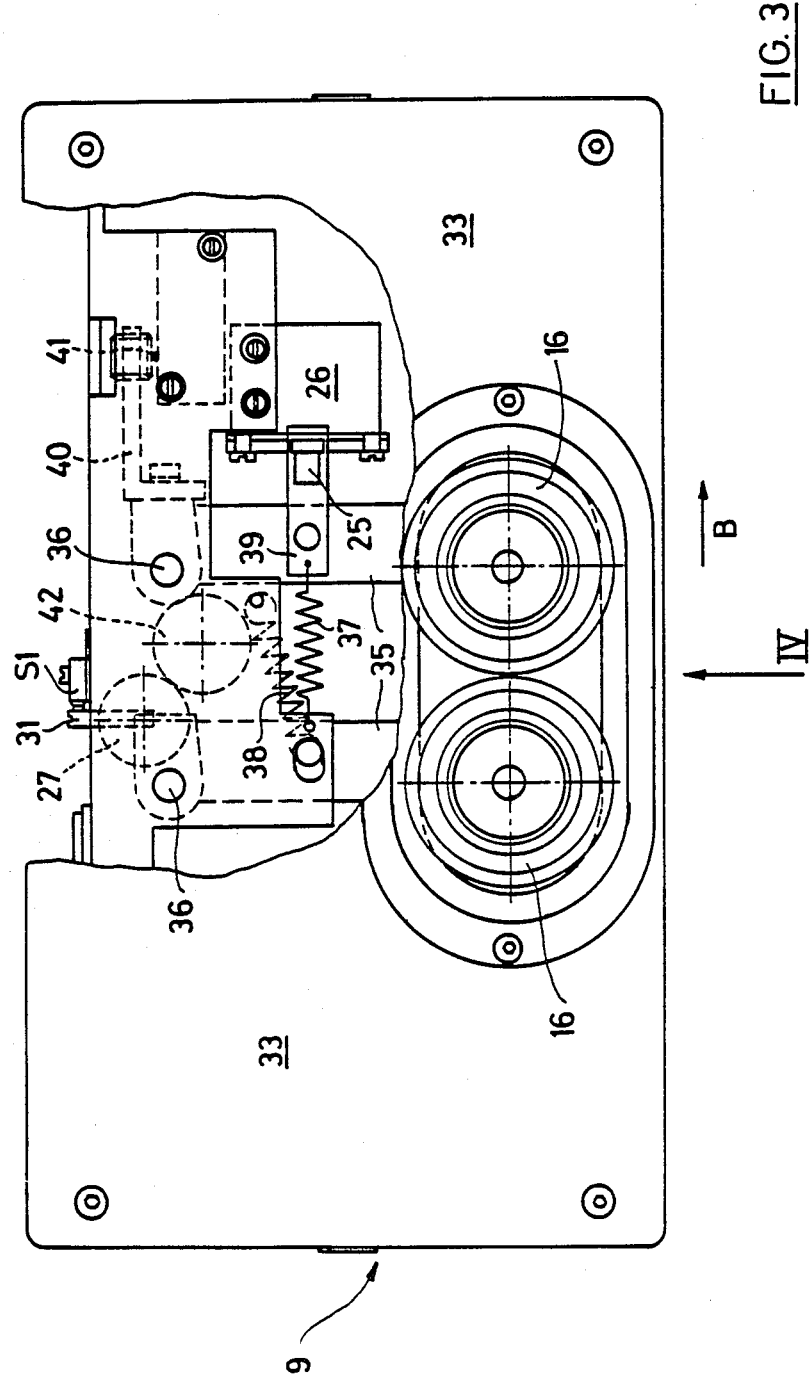
FIG. 3 is a front view of part of the measuring unit.
Figure 4:
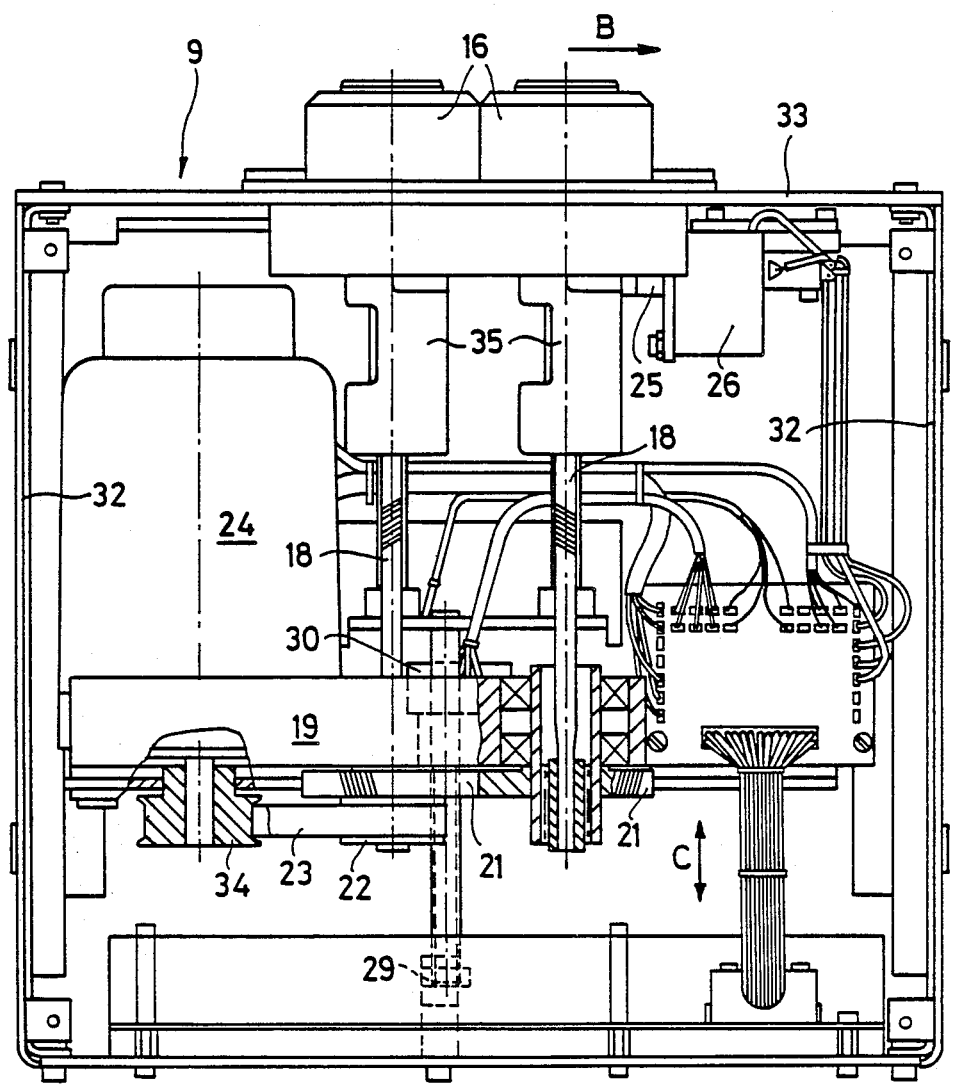
FIG. 4 is an elevational view in the direction of the arrow IV of FIG. 3 with the housing plate removed.

FIGS. 3 and 4 show an actual arrangement inside module 9 (FIG. 1) of the parts illustrated schematically in FIG. 2.

The module 9 includes, as illustrated, an approximately prismatic housing 32, which is pushed into the frame 14 (FIG. 1) and on which the two transport rollers 16 project from the front plate 33. The support plate 19 is a U shaped profile plate arranged parallel to the front plate 33 and mounted to be displaceable on the two side walls of the housing 32. The flexible shafts 18 are mounted in the support plate 19 and carry the two interengaging gear wheels 21 at the end projecting from the rear of the support plate 19. One of the two shafts, in the drawing the right hand shaft, carries the toothed belt pulley 22 which is driven b the belt pulley 34 of the drive motor 24 by way of the toothed belt 23, said drive motor being also mounted on the support plate 19.

The two flexible shafts 28 are each mounted in a support arm 35 in the region of the front plate 33, which support arms are arranged vertically in the housing 32. Each support arm 35 is pivotally mounted at its upper end on a bearing shaft 36 arranged parallel to the shafts 18, and each arm 35 carries a shaft 18 at its lower end. The two support arms 35 are drawn together by tension springs 37, 38, one on each arm. The left hand support arm 35 can be swung to the left by hand against the force of its tension spring 38, which may be necessary when a test material is exceptionally thick. A fish plate 39 is fixed to the right hand support arm 35 to carry the displacement member 25 (FIG. 2). Associated with this displacement member 25 is the electromagnet 26 which attracts the member 25 when energized so that the right hand transport roller 16 is swung away from the left hand roller. This takes place automatically when the test material P is inserted into the measuring unit 1 (FIG. 1).

A finger 40 which presses on a micro switch 41 when the transport rollers 16 are n contact, i.e. when a test is in progress, is attached to the top end of the automatically deflectable right hand support arm 35. As soon as the support arm 35 which carries the finger 40 is swung away, the finger 40 releases the micro switch 41. The micro switch 41 is a safety switch which switches off the drive motors 24 and 30 if they are in operation when the right hand transport roller 16 is swung away. Such deflection of the right hand transport roller 16 when in operation occurs if the test material is wound several times over the transport rollers due to the measuring unit 1 not being carefully monitored and the suction nozzle 12 operating at a low setting.

The driving motor 30 is also attached to the support plate 19, approximately at the level of the bearing shaft 36. This motor 30 drives the thread clutch 27 by means of a gear wheel 42 and thereby produces the displacement of the support plate 19 together with the parts attached thereto. The two end switches S1 and S2 are fixed with respect to the housing 32 and their actuating member 31 is also seen in FIG. 3.

Although the longitudinal displacement of the transport rollers 16 is brought about by a motor and opening of the gaps between them by an electromagnet in the particular example illustrated here, these movements are not limited to the driving means described and hydraulic or pneumatic drives could, of course, also be used. Pneumatic drives are particularly widely used in the textile industry.

Still other modifications and variations will suggest themselves to persons skilled in the art. It is intended therefore that the foregoing detailed description be understood as exemplary and that the scope of the invention be determined with reference to the following claims.

What is claimed is:

1. Apparatus for testing textile material such as yarns, rovings and slivers, comprising a measuring unit containing a guide device, a measuring instrument, a feed device and a draw off device for the test material, the feed device being formed by a pair of transport rollers resiliently pressed against one another, each of said transport rollers being mounted on a shaft, a gear wheel being mounted on each of the two shafts and being in engagement with one another to positively connect the two shafts together, and one of said shafts being connected to a drive means to provide a positive coupling of said drive means to both of the transport rollers.

2. Apparatus for testing textile material such as yarns, rovings and slivers, comprising a measuring unit containing a guide device, a measuring instrument, a feed device and a draw off device for the test material, the feed device being formed by a pair of transport rollers, both of which are positively connected to a drive means, and means for automatically temporarily increasing the distance between the axes of the two rollers so that the test material may be inserted between the rollers.

3. Apparatus according to claim 2, wherein said means for increasing the distance between the axes of the rollers includes a displacement device acting on one transport roller and by an actuating member associated with said displacement device.

4. Apparatus according to claim 3, wherein the actuating device is formed by an electromagnet.

5. Apparatus for testing textile material such as yarns, rovings and slivers, comprising a measuring unit containing a guide device, a measuring instrument, a feed device and a draw off device for the test material, the device being formed by a pair of transport rollers one of which is displaceable and both of which are mounted on shafts and drive means positively coupled to both of said shafts, said shaft carrying the displaceable transport roller being a flexible shaft at least over part of its length.

6. Apparatus according to claim 3, wherein the transport roller which is not automatically adjustable can be moved away from the adjustable transport roller by hand for the insertion of test material in the form of bands.

7. Apparatus according to claim 2, wherein means are provided for switching off the drive to the transport rollers when the axial distance between the rollers exceeds a certain value as the test material runs through between them.

8. Apparatus according to claim 7, wherein the last mentioned means are formed by an actuating element which is coupled to the automatically adjustable transport roller and by a switch associated with said actuating element.

9. Apparatus for testing textile material such as yarns, rovings and slivers, comprising a measuring unit containing a guide device, a measuring instrument, a feed device and a draw off device for the test material, which feed device is formed by a pair of transport rollers, between which the test material is passed, and means for effecting a relative motion between said rollers and the test material back and forth in the direction of the length of said transport rollers so that the location, along the lengths of the rollers, where said test material contacts said rollers shifts back and forth while said test material is being fed by said rollers.

10. Apparatus according to claim 9, wherein the transport rollers are connected to means for producing a reciprocating motion of the transport rollers along their axes.

11. Apparatus according to claim 10, including means for reversing the direction of movement of the transport rollers at the reversal points of their reciprocating motion.

12. Apparatus according to claim 11, wherein said transport rollers and carried by a slideably displaceable adjustment device and drive means are connected to said device for driving said device.

13. Apparatus according to claim 12, wherein the means for reversal of the direction of movement of the transport rollers are formed by switches arranged along the path of displacement of said displacement device and designed to be operated by this device and connected with the drive means.

14. Apparatus according to claim 13, wherein the driving direction is reversed when the switch is actuated.

15. Apparatus according to claim 14, wherein the drive is provided by a motor and a transmission connected thereto and wherein the switches are connected to the motor.

16. Apparatus according to one of the claim 9, additionally including means for automatically temporarily increasing the axial distance between the two transport rollers for insertion of the test material between them.

17. Apparatus according to claim 16, wherein the last mentioned means are formed by a displacement element acting on one transport roller and by an actuating device associated with said displacement element.

18. Apparatus according to claim 9, wherein the two transport rollers are positively connected with a driving means.

19. Apparatus according to claim 18, including means for switching off the drive to the transport rollers when the axial distance between the two rollers exceeds a certain value as the test material passes through between them.

* * * * *